United States Patent
Hogwood et al.

(10) Patent No.: US 10,786,007 B2
(45) Date of Patent: Sep. 29, 2020

(54) RESEALABLE AEROSOL-GENERATING ARTICLE

(71) Applicant: Philip Morris Products S.A., Neuchatel (CH)

(72) Inventors: Jonathan Hogwood, Royston (GB); Stuart Michael Ruan Jones, Royston (GB); John Antony Stephenson, Cambridge (GB); David Edington, St Albans (GB); Christopher Coulson, London (GB)

(73) Assignee: Philip Morris Products S.A., Neuchatel (CH)

( * ) Notice: Subject to any disclaimer, the term of this patent is extended or adjusted under 35 U.S.C. 154(b) by 356 days.

(21) Appl. No.: 15/555,737

(22) PCT Filed: Mar. 24, 2016

(86) PCT No.: PCT/EP2016/056578
§ 371 (c)(1),
(2) Date: Sep. 5, 2017

(87) PCT Pub. No.: WO2016/156216
PCT Pub. Date: Oct. 6, 2016

(65) Prior Publication Data
US 2018/0042305 A1      Feb. 15, 2018

(30) Foreign Application Priority Data
Mar. 27, 2015   (EP) ..................................... 15161536

(51) Int. Cl.
*A24F 47/00*     (2020.01)
*A61M 15/06*     (2006.01)
(Continued)

(52) U.S. Cl.
CPC .......... *A24F 47/008* (2013.01); *A61M 11/041* (2013.01); *A61M 11/042* (2014.02); *A61M 15/0001* (2014.02); *A61M 15/06* (2013.01)

(58) Field of Classification Search
None
See application file for complete search history.

(56) References Cited

U.S. PATENT DOCUMENTS

2007/0062548 A1 *   3/2007   Horstmann ........... A24F 47/002
                                                       131/270
2009/0095311 A1     4/2009   Han
(Continued)

FOREIGN PATENT DOCUMENTS

CN        1889861 A      1/2007
CN       102894486 A      1/2013
(Continued)

OTHER PUBLICATIONS

European Office Action dated Aug. 6, 2018 in European Patent Application No. 16711666.4, 5 pages.
(Continued)

*Primary Examiner* — Bradley H Philips
*Assistant Examiner* — Savannah L Gabriel
(74) *Attorney, Agent, or Firm* — Oblon, McClelland, Maier & Neustadt, L.L.P.

(57) ABSTRACT

An aerosol-forming article is provided, including an airflow inlet and an airflow outlet; a medicament source and a volatile delivery enhancing compound source disposed between the airflow inlet and the airflow outlet, and a moveable portion moveable between an open position in which the medicament source and the volatile delivery enhancing compound source are in fluid communication with both the airflow inlet and the airflow outlet, and a closed position in which each of the medicament source and (Continued)

the volatile delivery enhancing compound source is in communication with only one or none of the airflow inlet and the airflow outlet.

10 Claims, 2 Drawing Sheets

(51) Int. Cl.
 *A61M 11/04* (2006.01)
 *A61M 15/00* (2006.01)

(56) References Cited

U.S. PATENT DOCUMENTS

| | | |
|---|---|---|
| 2009/0126745 A1 | 5/2009 | Hon |
| 2011/0209717 A1 | 9/2011 | Han |
| 2012/0255567 A1* | 10/2012 | Rose .................. A61K 9/12 131/273 |
| 2013/0125906 A1 | 5/2013 | Hon |
| 2013/0139833 A1 | 6/2013 | Hon |
| 2013/0276798 A1 | 10/2013 | Hon |
| 2013/0306064 A1* | 11/2013 | Thorens ................ A61M 15/06 128/202.21 |
| 2014/0209110 A1 | 7/2014 | Hon |
| 2015/0013697 A1 | 1/2015 | Mironov |
| 2015/0196060 A1 | 7/2015 | Wensley et al. |
| 2015/0250230 A1 | 9/2015 | Hon |
| 2015/0250231 A1 | 9/2015 | Hon |
| 2015/0250232 A1 | 9/2015 | Hon |

FOREIGN PATENT DOCUMENTS

| | | |
|---|---|---|
| CN | 103237469 A1 | 8/2013 |
| EP | 2 022 349 A1 | 2/2009 |
| RU | 2010 148 832 A | 6/2012 |
| WO | WO 2006/121610 A1 | 10/2006 |
| WO | WO 2011/034723 A1 | 3/2011 |
| WO | WO 2013/120854 A1 | 8/2013 |
| WO | WO 2014/140320 A1 | 9/2014 |
| WO | WO 2014/187770 A2 | 11/2014 |
| WO | WO 2015/000974 A1 | 1/2015 |
| WO | WO 2015/042412 A1 | 3/2015 |
| WO | WO 2015/082652 A1 | 6/2015 |

OTHER PUBLICATIONS

International Search Report and Written Opinion dated Jun. 14, 2016 in PCT/EP2016/056578, filed Mar. 24, 2016.
Combined Russian Decision to Grant and Search Report dated Apr. 23, 2019 in Russian Patent Application No. 2017134788 (with English translation of Decision to Grant only), 14 pages.
Combined Chinese Office Action and Search Report dated Oct. 28, 2019, in Patent Application No. 201680015125.9, 13 pages (with English translation).
Chinese Office Action and Search Report dated Jun. 30, 2020 in corresponding Chinese Application No. 201680015125.9 (with English translation), 13 pages.

* cited by examiner

RESEALABLE AEROSOL-GENERATING ARTICLE

The present invention relates to an aerosol-generating system for generating an aerosol comprising a medicament. The invention finds particular application as an aerosol-generating system for generating an aerosol comprising nicotine salt particles.

Some devices for delivering nicotine or other medicaments to a user comprise a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. Therefore, to prevent premature evaporation of the volatile delivery enhancing compound and the nicotine both sources are usually sealed with one or more frangible seals that a user must break to use the aerosol-generating system. However, once the one or more frangible seals are broken the user typically has only a limited time to use the aerosol-generating system until the volatile delivery enhancing compound and the nicotine have evaporated from the system.

In devices comprising a nicotine or other medicament source and a volatile delivery enhancing compound source it would be desirable to allow a consumer to use the device over an extended period of time with minimal evaporative escape of the medicament and the volatile delivery enhancing compound source.

The present invention provides an aerosol-forming article comprising an airflow inlet and an airflow outlet. The aerosol-forming article further comprises a medicament source and a volatile delivery enhancing compound source positioned between the airflow inlet and the airflow outlet, and a moveable portion. The moveable portion is moveable between an open position in which the medicament source and the volatile delivery enhancing compound source are in fluid communication with both the airflow inlet and the airflow outlet, and a closed position in which each of the medicament source and the volatile delivery enhancing compound source is in communication with only one or none of the airflow inlet and airflow outlet.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. The aerosol-generating article may comprise an aerosol-forming substrate capable of releasing upon heating volatile compounds, which can form an aerosol. An aerosol-generating article may be entirely consumable and mainly comprise a medicament source and a volatile delivery enhancing compound. The aerosol-generating article may comprise a reusable portion, such as a mouthpiece configured for attachment to an aerosol-generating device, and a consumable portion comprising the medicament and volatile delivery enhancing compound sources and configured for insertion into the reusable portion.

As used herein, the term "aerosol-generating system" refers to a combination of an aerosol-generating article with an aerosol-generating device.

As used herein, the term "medicament source" refers to a source of one or more volatile compounds intended for delivery to the lungs of a user. In preferred embodiments, the medicament source comprises a nicotine source.

As used herein, the term "volatile delivery enhancing compound source" refers to a source of one or more volatile compounds that react with the medicament source in the gas phase to aid delivery of the one or more compounds from the medicament source to the user.

By providing a moveable portion that can prevent fluid communication between each of the medicament and volatile delivery enhancing compound sources and one or both of the airflow inlet and airflow outlet, an aerosol-generating article in accordance with the present invention can reduce or eliminate spoiling and evaporative escape of the medicament and the volatile delivery enhancing compound. Accordingly, after first using the article it is not necessary for a user to consume all of the medicament and the volatile delivery enhancing compound immediately. Instead, the user can consume part of the medicament and the volatile delivery enhancing compound and then close the moveable portion of the aerosol-generating article until a later time at which the user wishes to further use the article.

The aerosol-forming article may further comprise an inner portion on which the medicament source and the volatile delivery enhancing compound source are provided, wherein the moveable portion comprises an outer housing containing the inner portion, the outer housing configured for relative movement with respect to the inner portion. The outer housing may be a tubular outer housing and the inner portion may be a tubular or cylindrical inner portion contained within the outer housing. The outer housing may be configured for relative rotational movement with respect to the inner portion.

In those embodiments comprising an outer housing moveable with respect to an inner portion, the aerosol-forming article may comprise at least one seal. The at least one seal may comprise a first end secured to an inner surface of the outer housing and a second end secured to the inner portion. The inner surface of the outer housing may be spaced apart from the inner portion and the outer housing may be moveable between the closed position in which the at least one seal covers the medicament source and the volatile delivery enhancing compound source, and the open position in which the medicament source and the volatile delivery enhancing compound source are at least partially uncovered.

In those embodiments in which the inner portion is a tubular or cylindrical inner portion it may further comprise a first recess in which the medicament source is provided and a second recess in which the volatile delivery enhancing compound source is provided. The at least one seal may comprise at least one portion of sheet material comprising the first end secured to the inner surface of the outer housing and the second end secured to the inner portion adjacent the recesses.

In those embodiments in which the outer housing is a tubular outer housing rotatable in a circumferential direction relative to a tubular or cylindrical inner portion, the first end of the sheet material may overlie the inner portion adjacent a first side of the recesses when outer housing is in the closed position and the second end of the sheet material may be secured to the inner portion adjacent a second side of the recesses, wherein the first and second sides are spaced apart in the circumferential direction with the recesses therebetween. When the outer housing is rotated in the circumferential direction into the open position, the first end of the sheet material overlies the inner portion adjacent the second side of the recesses so that the recesses are no longer cover by the sheet material.

The sheet material is preferably a non-permeable inelastic material, such as a metal foil or a substantially inelastic plastic. The at least one portion of sheet material may comprise a first portion of sheet material for sealing the recess containing the medicament source and a second portion of sheet material for sealing the recess containing the volatile delivery enhancing compound source. The at least one portion of sheet material may comprise a resealable adhesive provided on a surface of the sheet material that contacts the inner portion when the outer housing is in the closed position.

As an alternative to using one or more portions of a sheet material to form a seal, the outer housing can instead be configured so that it is moveable between the closed position in which an inner surface of the outer housing contacts the inner portion and covers the medicament source and the volatile delivery enhancing compound source, and the open position in which the inner surface of the outer housing is spaced apart from the inner portion so that the medicament source and the volatile delivery enhancing compound source are uncovered. The inner surface of the outer housing may comprise a tapered portion.

The outer housing may be a tubular outer housing and the inner portion may be a tubular or cylindrical inner portion, wherein the outer housing is rotatable in a circumferential direction relative to the inner portion. The inner portion preferably comprises a first recess in which the medicament source is provided and a second recess in which the volatile delivery enhancing compound source is provided. The inner surface of the outer housing may contact the inner portion around the perimeter of each recess when the outer housing is in the closed position so that each recess is sealed.

In those embodiments in which the outer housing is rotatable in a circumferential direction with respect to the inner portion, the outer housing may comprise a circular cross-sectional shape having a centre that is offset from the centre of rotation of the outer housing. In this case, the eccentric rotation of the outer housing provides the contact between the outer housing and the inner portion when the outer housing is moved from the open to the closed position. The outer housing or the inner portion may have a non-circular cross-sectional shape, such as an ellipse or an oval, to achieve the same effect.

As an alternative to providing an outer housing that is moveable with respect to an inner portion as described above, the aerosol forming article according to the present invention can instead comprise an outer housing in which the airflow inlet and the airflow outlet are provided, and an airflow channel contained in the outer housing and extending between the airflow inlet and the airflow outlet. The medicament source and the volatile delivery enhancing compound source may be provided within the airflow channel and the moveable portion may be moveable between the closed position in which the moveable portion obstructs the airflow channel to prevent airflow between the airflow inlet and the airflow outlet through the airflow channel, and the open position in which the airflow channel is unobstructed.

Preferably, the moveable portion comprises a first end configured to obstruct the airflow channel when the moveable portion is in the closed position, and a second end extending through an aperture in the outer housing to allow a user to access the second end of the movable portion to move the moveable portion between the open and closed positions. The moveable portion may comprise a push button extending through the aperture in the outer housing. The push button preferably includes a locking mechanism to selectively retain the push button in one or both of the open and closed positions. The push button may comprise a biasing means, such as a spring, to bias the push button towards the open position, and a locking mechanism to selectively retain the push button in the closed position.

In any of the embodiments described above, the aerosol-generating article may further comprise one or more frangible barriers providing an initial seal to one or both of the medicament source and the volatile delivery enhancing compound source. The seal provided by the frangible barriers may be separate from the resealing effect provided by the moveable portion. It may be necessary to irreversibly pierce or otherwise rupture the frangible barriers before the aerosol-generating article can be used. At least one of the medicament and the volatile delivery enhancing compound may be a liquid sealed in a blister that forms a frangible barrier. In those embodiments comprising one or more frangible barriers, the aerosol-generating article may include at least one piercing element or rupturing portion to break the frangible barrier. Alternatively, the at least one piercing element or rupturing portion may form part of an aerosol-generative device used with the aerosol-generating article.

In this regard, the present invention extends to an aerosol-generating system comprising an aerosol-generating article in accordance with any of the embodiments described above and an aerosol-generating device, the aerosol-generating device comprising a heater element.

In any of the embodiments described above, the medicament source and the volatile delivery enhancing compound source are preferably arranged in series within the aerosol-generating article.

As used herein, by "series" it is meant that the medicament source and the volatile delivery enhancing compound source are arranged within the aerosol-generating article so that in use an air stream drawn through the aerosol-generating article passes through one of the medicament source and the volatile delivery enhancing compound source and then passes through the other of the medicament source and the volatile delivery enhancing compound source. Preferably, the medicament source is upstream of the volatile delivery enhancing compound source so that in use medicament vapour is released from the medicament source into the air stream drawn through the aerosol-generating article and volatile delivery enhancing compound vapour is released from the volatile delivery enhancing compound source into the medicament-containing air stream drawn through the aerosol-generating article. The medicament vapour reacts with the volatile delivery enhancing compound vapour in the gas phase to form an aerosol, which is delivered to a user.

The medicament source and the volatile delivery enhancing compound source may be arranged in parallel within the aerosol-generating article.

The volatile delivery enhancing compound preferably has a vapour pressure of at least about 20 Pa, more preferably at least about 50 Pa, more preferably at least about 75 Pa, most preferably at least 100 Pa. Unless otherwise stated, all vapour pressures referred to herein are vapour pressures at 25° C. measured in accordance with ASTM E1194-07.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. The volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. The volatile delivery enhancing compound may comprise a non-aqueous solution of one or more compounds.

The volatile delivery enhancing compound may comprise two or more different volatile compounds. The volatile delivery enhancing compound may comprise a mixture of two or more different volatile liquid compounds.

The volatile delivery enhancing compound may comprise one or more non-volatile compounds and one or more volatile compounds. The volatile delivery enhancing compound may comprise a solution of one or more non-volatile compounds in a volatile solvent or a mixture of one or more non-volatile liquid compounds and one or more volatile liquid compounds.

The volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid. The volatile delivery enhancing compound may comprise lactic acid. Other suitable acids includes aspartic acid, glutamic acid, salicylic acid, tartaric acid, gallic acid, levulinic acid, acetic acid, malic acid, citric acid, oxalic acid, sulphuric acid, palmitic acid, and alginic acid.

Preferably, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. In a particularly preferred embodiment, the volatile delivery enhancing compound comprises pyruvic acid.

The volatile delivery enhancing compound source comprises a sorption element and a volatile delivery enhancing compound sorbed on the sorption element. The volatile delivery enhancing compound may be sorbed onto the sorption element during manufacture and the sorption element may be sealed. The volatile delivery enhancing compound may be stored separately from the sorption element, for example in a blister on or adjacent the sorption element. The volatile delivery enhancing compound source may be formed when the volatile delivery enhancing compound is released and sorbed onto the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. The sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the sorption element is a porous sorption element.

The sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

The size, shape and composition of the sorption element may be chosen to allow a desired amount of volatile delivery enhancing compound to be sorbed on the sorption element.

Preferably, between about 20 μl and about 200 μl, more preferably between about 40 μl and about 150 μl, most preferably between about 50 μl and about 100 μl of the volatile delivery enhancing compound is sorbed on the sorption element.

The sorption element advantageously acts as a reservoir for the volatile delivery enhancing compound.

Preferably, the medicament has a melting point below about 150 degrees Celsius.

Alternatively or in addition, preferably the medicament has a boiling point below about 300 degrees Celsius.

Preferably, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(l-methyl-2-pyrrolidinyl)isoxazole (ABT 418) and (±)-2-(3-Pyridinyl)-I-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

Preferably, the medicament source comprises a nicotine source. The nicotine source may comprise one or more of nicotine, nicotine base, a nicotine salt, such as nicotine-HCl, nicotine-bitartrate, or nicotine-tartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

The nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

The nicotine source may comprise an aqueous solution of nicotine, nicotine base, a nicotine salt or a nicotine derivative and an electrolyte forming compound.

The nicotine source may further comprise other components including, but not limited to, natural flavours, artificial flavours and antioxidants.

The medicament source may comprise a sorption element as described above and a medicament sorbed on the sorption element. The medicament may be sorbed onto the sorption element during manufacture and the sorption element may be sealed. The medicament may be stored separately from the sorption element, for example in a blister on or adjacent the sorption element. The medicament source is formed when the medicament is released and sorbed onto the sorption element.

The aerosol-generating device is preferably configured to heat the medicament source and the volatile delivery enhancing compound source of the aerosol-generating article so that the medicament source of the aerosol-generating article has a higher temperature than the volatile delivery enhancing compound source of the aerosol-generating article. The aerosol-generating device is configured to substantially simultaneously heat the medicament source and the volatile delivery enhancing compound source of the aerosol-generating article.

In any of the embodiments described above, the aerosol-generating device and the aerosol-generating article may be configured to heat the medicament source to a first temperature and to heat the volatile delivery enhancing compound source to a second temperature, wherein the first temperature is at least about 50 degrees Celsius higher than the second temperature, preferably at least about 70 degrees Celsius higher than the second temperature, most preferably at least about 80 degrees Celsius higher than the second temperature. Additionally, or alternatively, the first temperature is preferably no more than about 100 degrees Celsius higher than the second temperature. Preferably, the temperature difference between the first and second temperatures is between about 50 and about 100 degrees Celsius, more preferably between about 60 and about 100 degrees Celsius, most preferably between about 80 and about 100 degrees Celsius.

In any of the embodiments described above, the aerosol-generating device and the aerosol-generating article may be configured to heat the volatile delivery enhancing compound source to a temperature of at least about 30 degrees Celsius. Additionally, or alternatively, the aerosol-generating device and the aerosol-generating article may be configured to heat the volatile delivery enhancing compound source to a temperature of less than about 100 degrees Celsius, preferably less than about 70 degrees Celsius. Preferably, the aerosol-generating device and the aerosol-generating article are configured to heat the volatile delivery enhancing compound source to a temperature of between about 30 and about 100 degrees Celsius, more preferably between about 30 and about 70 degrees Celsius.

In any of the embodiments described above, the aerosol-generating device and the aerosol-generating article may be configured to heat the medicament source to a temperature of at least about 50 degrees Celsius. Additionally, or alternatively, the aerosol-generating device and the aerosol-generating article may be configured to heat the medicament source to a temperature of less than about 150 degrees Celsius, preferably less than about 100 degrees Celsius. Preferably, the aerosol-generating device and the aerosol-generating article are configured to heat the medicament source to a temperature of between about 50 and about 150 degrees Celsius, more preferably between about 50 and about 100 degrees Celsius.

The aerosol-generating device may further comprise a controller configured to control a supply of power to the heater element.

The aerosol-generating device may further comprise a power supply for supplying power to the heater element and a controller configured to control a supply of power from the power supply to the heater element. The controller of the aerosol-generating device may be configured to control a supply of power from an external power supply to the heater element.

The heater element may be an electric heater element powered by an electric power supply. Where the heater element is an electric heater element, the aerosol-generating device may further comprise an electric power supply and a controller comprising electronic circuitry configured to control the supply of electric power from the electric power supply to the electric heater element.

The power supply may be a DC voltage source. Preferably, the power supply is a battery. The power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating articles.

The heater element may be a non-electric heater, such as a chemical heating means. The heater element of the aerosol-generating device preferably comprises a single heater element to simplify the construction of the aerosol-generating device. Differential heating of the medicament source and the volatile delivery enhancing compound source can be achieved by contacting at least one of the sources with a resilient member, which in turn is biased against the heater element.

The heater element may have any suitable shape. Preferably, the heater element is an elongate heater element. Preferably, the elongate heater element has a width that is greater than the thickness of the heater element so that the heater element forms a heater blade.

Preferably, the heater element is heated electrically. However, other heating schemes may be used to heat the heater element. The heater element may be heated by conduction from another heat source. The heater element may comprise an infra-red heater element, a photonic source, or an inductive heater element.

The heater element may comprise a heat sink, or heat reservoir comprising a material capable of absorbing and storing heat and subsequently releasing the heat over time to the aerosol-forming article. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, a metal salt, a mixture of eutectic salts or an alloy.

Preferably, the heater element preferably comprises an electrically resistive material. The heater element may comprise a non-elastic material, for example a ceramic sintered material, such as alumina ($Al_2O_3$) and silicon nitride ($Si_3N_4$), or printed circuit board or silicon rubber. Alternatively, the heater element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required.

The aerosol-generating device may comprise one or more temperature sensors configured to sense the temperature of at least one of the heater element, the medicament source and the volatile delivery enhancing compound source. In such embodiments, the controller may be configured to control a supply of power to the heater element based on the sensed temperature.

The heater element may be formed using a metal having a defined relationship between temperature and resistivity. In such embodiments, the metal may be formed as a track between two layers of suitable insulating materials. A heater element formed in this manner may be used both as a heater and a temperature sensor.

The invention will now be further described, by way of example only, with reference to the accompanying drawings in which.

Like reference numerals will be used to designate like parts in the following description of the drawings.

Figure 1:
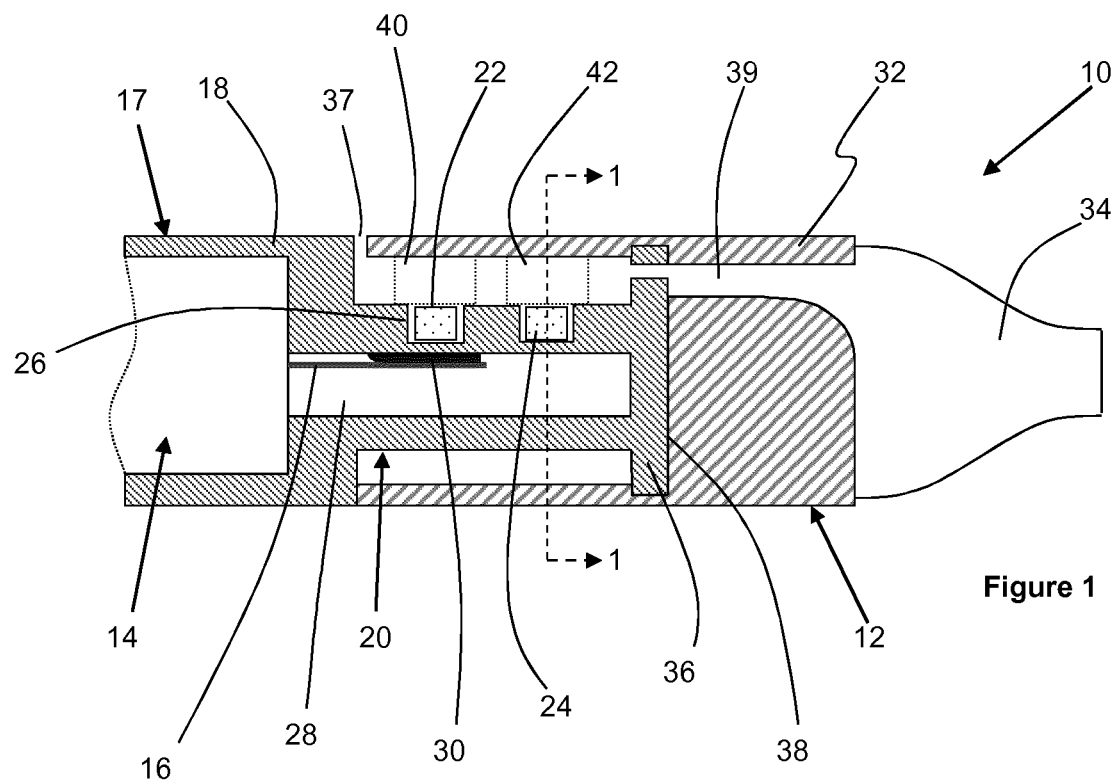
FIG. 1 shows an aerosol-generating system comprising an aerosol-generating article in accordance with a first embodiment of the present invention.

FIG. 1 shows an aerosol-generating system 10 comprising an aerosol-generating article 12 in accordance with an embodiment of the invention in combination with an aerosol-generating device 14. The aerosol-generating device 14 comprises heater element 16 in the form of a heater blade. The heater element 16 is electrically heated and the aerosol-generating device may comprise a power source and control electronics, as is known in the art.

The aerosol-generating article 12 comprises an upstream body portion 17 comprising an upstream portion 18 connected to the aerosol-generating device 14 and a downstream portion 20 on which a medicament source 22 and a volatile delivery enhancing compound source 24 are provided. Each of the medicament source 22 and the volatile delivery enhancing compound source 24 is provided in a recess 26 in a surface of the downstream portion 20.

The heater blade 16 of the aerosol-generating device 14 is received within a cavity 28 in the downstream portion 20 of the upstream body portion 17. A heat conductive plate 30 is provided on a surface of the downstream portion 20 inside the cavity 28 and adjacent the medicament source 22. The heater element 16 contacts the heat conductive plate 30 so that during operation of the device heat is transferred to the medicament source 22. The heat conductive plate 30 does not extend underneath the volatile delivery enhancing compound source 24 so that the volatile delivery enhancing compound source 24 is heated to a lower temperature than the medicament source 22.

The aerosol-generating article 12 further comprises a downstream body portion 32 and a mouthpiece 34 extending from a downstream end of the downstream body portion 32. A circular flange 36 on the upstream body portion 17 is positioned within an annular slot 38 in the downstream body portion 32 so that the downstream body portion 32 is rotatable about the circular flange 36. An airflow inlet 37 is defined between the upstream and downstream body portions 17 and 32 and the mouthpiece 34 provides an airflow outlet. An airflow passage 39 extends between the airflow inlet 37 and the mouthpiece 34.

Figures 2, 3:
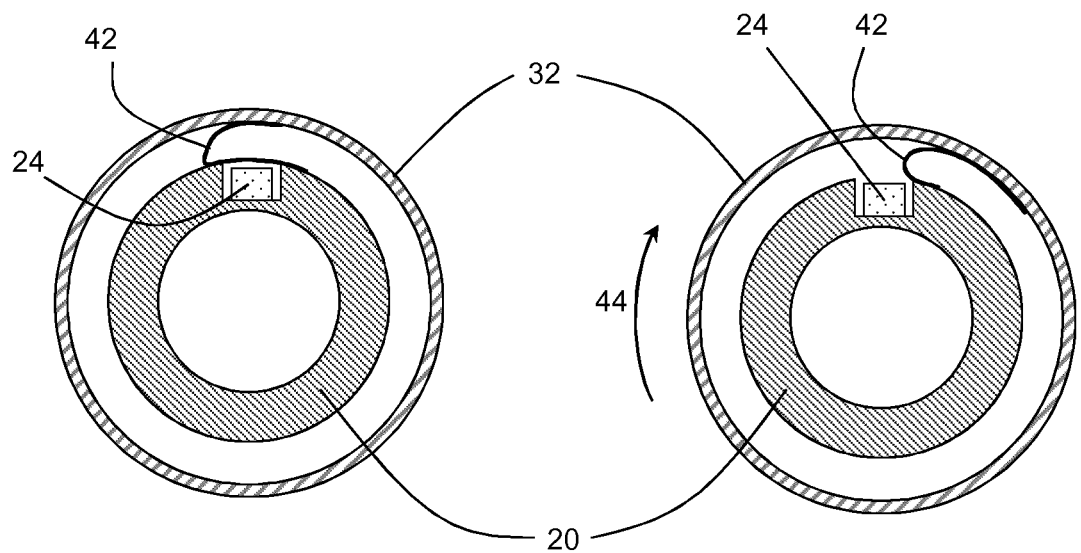
FIG. 2 shows a transverse cross section of the aerosol-generating system of FIG. 1 taken along line 1-1, with the moveable portion in the closed position.
FIG. 3 shows a transverse cross section of the aerosol-generating system of FIG. 1 taken along line 1-1, with the moveable portion in the open position.

As shown more clearly in FIGS. 2 and 3, which show transverse cross-sectional views of the aerosol-generating article 12 taken along line 1-1 in FIG. 1, first and second foil seals 40 and 42 each comprise a first end secured to the downstream body portion 32 and a second end secured to the downstream portion 20 of the upstream body portion 17. When the downstream body portion 32 is in the closed position, as shown in FIG. 2, the first and second foil seals 40 and 42 cover the recesses 26 in which the medicament source 22 and the volatile delivery enhancing compound source 24 are provided. Rotating the downstream body portion 32 in the circumferential direction 44 into the open position, as shown in FIG. 3, peels the foil seals 40 and 42 away from the recesses 26 to expose the medicament source 22 and the volatile delivery enhancing compound source 24. The downstream body portion 32 can be moved between the open and closed positions to repeatedly unseal and seal the recesses 26.

Figure 4:
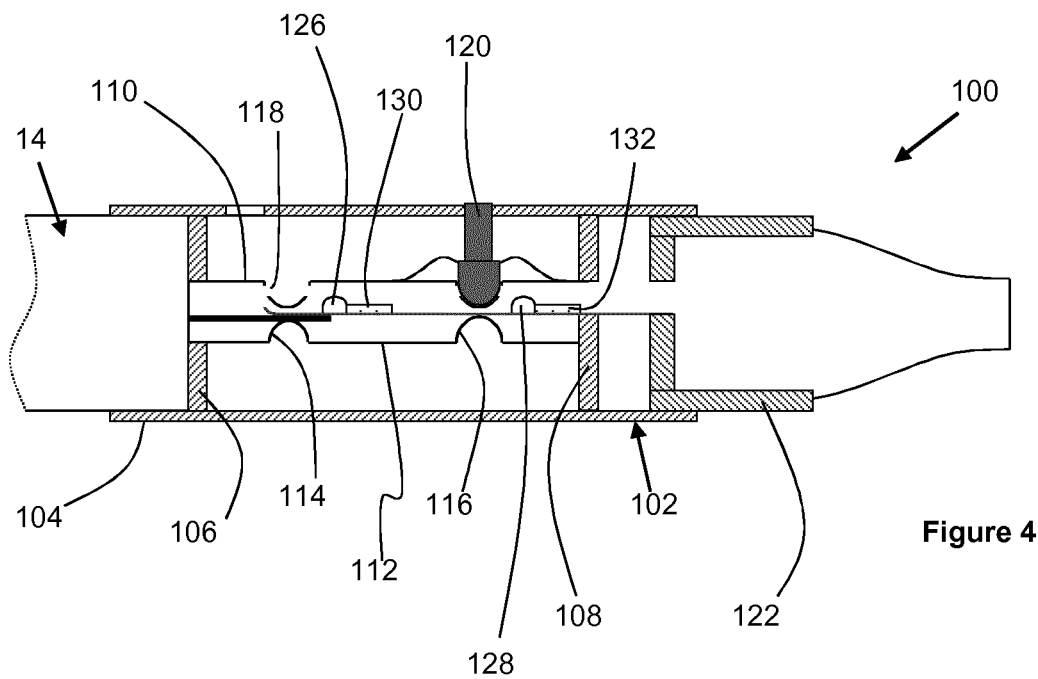
FIG. 4 shows an aerosol-generating system comprising an aerosol-generating article in accordance with a second embodiment of the present invention, with the moveable portion in the closed position.
Figure 5:
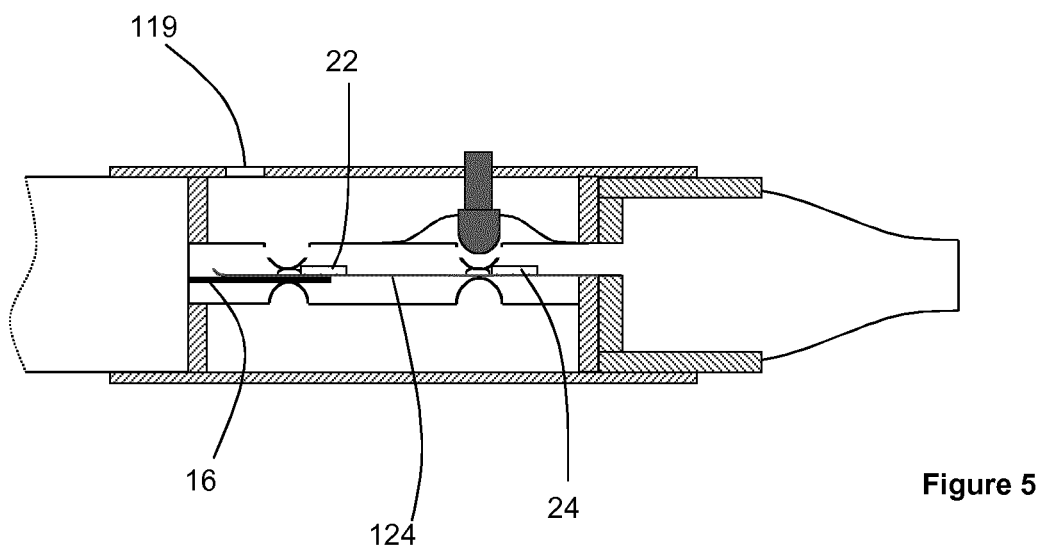
FIG. 5 shows the aerosol-generating system of FIG. 4 with the moveable portion in the open position.

FIGS. 4 and 5 show an aerosol-generating system 100 comprising an aerosol-generating article 102 in accordance with a second embodiment of the invention and an aerosol-generating device 14, as described with respect to the previous embodiment.

The aerosol-generating article 102 comprises a tubular outer housing 104 in which an upstream annular stopper 106 and a downstream annular stopper 108 are mounted. Extending between the annular stoppers 106 and 108 are a first rupturing member 110 and a second rupturing member 112 each comprising an elongate plate having an upstream protrusion 114 and a downstream protrusion 116. The protrusions 114 and 116 on the first rupturing member 110 each comprise one or more airflow apertures 118 to allow airflow to enter the airflow passage defined in the space between the first and second rupturing members 110 and 112. An airflow inlet 119 in the outer housing 104 allows air to flow into the aerosol-generating article 102.

A push-button 120 shaped for insertion into the recess forming the downstream protrusion 116 on the first rupturing member 110 extends through an aperture in the outer housing 104. The push-button 120 allows a user to selectively open and close the airflow apertures 118 in the upstream protrusion of the first rupturing member 110 to prevent or allow the flow of air through the aerosol-generating article 102 after the aerosol-generating article 102 has been activated. The push-button 120 is shown in the closed position in FIG. 4 and the open position in FIG. 5.

The aerosol-generating article 102 further comprises a tubular segment 122 slidably received within the downstream end of the outer housing 104. A mouthpiece 34, as described previously, extends downstream from the tubular segment 122. A resilient member 124 extends upstream from the tubular segment 122 and is positioned between the first and second rupturing members 110 and 812. The resilient member 124 is resiliently biased against the heater element 16 of the aerosol-generating device 14. The resilient member 124 is formed from a thermally conductive resilient material, such as a metal, capable of withstanding the operating temperature of the heater element 16.

A medicament blister 126 is provided on the resilient member 124, the medicament blister 126 comprising a blister containing a liquid medicament, such as nicotine. The blister forms a frangible barrier containing the liquid medicament. Similarly, a volatile delivery enhancing compound blister 128 is provided on the resilient member 124, the volatile delivery enhancing compound blister 128 comprising a blister containing a liquid volatile delivery enhancing compound, such as pyruvic acid. The blister forms a frangible barrier containing the liquid volatile delivery enhancing compound. First and second sorption elements 130 and 132 are provided on the resilient member 124 adjacent the medicament and volatile delivery enhancing compound blisters 126 and 128 respectively.

To activate the aerosol-generating article 102, a user slides the tubular segment 122 into the outer housing 104 until the tubular segment abuts the downstream annular stopper 108. Sliding the tubular segment 122 into the outer housing 104 also slides the resilient member 124 further into the housing outer 104 so that the medicament and volatile delivery enhancing compound blisters 126 and 128 are crushed and ruptured between the upstream and downstream protrusions 114 and 116 of the first and second rupturing members 110 and 112, as shown in FIG. 5. Rupturing the blisters causes at least some of the medicament and the volatile delivery enhancing compound source to be sorbed onto the first and second sorption elements 130 and 132 respectively. The first sorption element 130 with at least some of the medicament sorbed thereon forms a medicament source 22 that contacts the resilient member 124. Similarly, the second sorption element 132 with at least some of the volatile delivery enhancing compound sorbed thereon forms a volatile delivery enhancing compound source 24 that contacts the resilient member 124 downstream from the medicament source 22.

During operation of the aerosol-generating system 100, the heater element 16 heats the medicament source 22 and the volatile delivery enhancing compound source 24 via the resilient member 124. The medicament source 22 is positioned on the resilient member 124 upstream from the volatile delivery enhancing compound source 24 and therefore closer to the heater element 16. Accordingly, the heater element 16 heats the medicament source 22 to a higher temperature than the volatile delivery enhancing compound source 24.

The invention claimed is:

1. An aerosol-forming article, comprising:
   an airflow inlet and an airflow outlet;
   a medicament source and a volatile delivery enhancing compound source disposed between the airflow inlet and the airflow outlet;
   a moveable portion moveable between an open position in which the medicament source and the volatile delivery enhancing compound source are in fluid communication with both the airflow inlet and the airflow outlet, and a closed position in which each of the medicament source and the volatile delivery enhancing compound source is in communication with only one or none of the airflow inlet and the airflow outlet;
   an inner portion on which the medicament source and the volatile delivery enhancing compound source are disposed, wherein the moveable portion comprises an outer housing containing the inner portion, the outer housing configured for relative movement with respect to the inner portion; and
   at least one seal comprising a first end secured to an inner surface of the outer housing and a second end secured to the inner portion,
   wherein the inner surface of the outer housing is spaced apart from the inner portion, and wherein the outer housing is moveable between the closed position in which the at least one seal covers the medicament source and the volatile delivery enhancing compound source, and the open position in which the medicament source and the volatile delivery enhancing compound source are at least partially uncovered.

2. The aerosol-forming article according to claim 1, wherein the outer housing is moveable between the closed position in which an inner surface of the outer housing contacts the inner portion and covers the medicament source and the volatile delivery enhancing compound source, and the open position in which the inner surface of the outer housing is spaced apart from the inner portion so that the medicament source and the volatile delivery enhancing compound source are uncovered.

3. The aerosol-forming article according to claim 2, wherein the inner surface of the outer housing comprises a tapered portion.

4. The aerosol-forming article according to claim 1, further comprising:
   an outer housing in which the airflow inlet and the airflow outlet are disposed; and
   an airflow channel contained in the outer housing and extending between the airflow inlet and the airflow outlet,
   wherein the medicament source and the volatile delivery enhancing compound source are disposed within the airflow channel, and
   wherein the moveable portion is moveable between the closed position in which the moveable portion obstructs the airflow channel to prevent airflow between the airflow inlet and the airflow outlet through the airflow channel, and the open position in which the airflow channel is unobstructed.

5. The aerosol-forming article according to claim 4, wherein the moveable portion comprises a first end configured to obstruct the airflow channel when the moveable portion is in the closed position, and a second end extending through an aperture in the outer housing to allow a user to access the second end of the movable portion to move the moveable portion between the open and closed positions.

6. The aerosol-generating article according to claim 1, wherein the medicament source comprises a nicotine source.

7. The aerosol-generating article according to claim 1, wherein the volatile delivery enhancing compound source comprises an acid.

8. An aerosol-generating system comprising an aerosol-forming article according to claim 1 in combination with an aerosol-generating device comprising a heater element.

9. The aerosol-generating system according to claim 8, wherein the aerosol-generating device and the aerosol-generating article are configured to heat the medicament source to a temperature of between 50 degrees Celsius and 150 degrees Celsius.

10. The aerosol-generating system according to claim 8, wherein the aerosol-generating device and the aerosol-generating article are configured to heat the volatile delivery enhancing compound source to a temperature of between 30 degrees Celsius and 100 degrees Celsius.

* * * * *